(12) United States Patent
Kullok et al.

(10) Patent No.: US 8,442,632 B2
(45) Date of Patent: May 14, 2013

(54) METHOD AND APPARATUS FOR AFFECTING THE AUTONOMIC NERVOUS SYSTEM

(76) Inventors: Saul Kullok, Jerusalem (IL); Yossi Kullok, Jerusalem (IL)

( * ) Notice: Subject to any disclaimer, the term of this patent is extended or adjusted under 35 U.S.C. 154(b) by 1081 days.

(21) Appl. No.: 12/169,914

(22) Filed: Jul. 9, 2008

(65) Prior Publication Data

US 2008/0269821 A1    Oct. 30, 2008

Related U.S. Application Data

(63) Continuation of application No. 10/778,306, filed on Feb. 17, 2004, now abandoned, which is a continuation of application No. 09/715,046, filed on Nov. 20, 2000, now abandoned, which is a continuation of application No. 09/176,566, filed on Oct. 21, 1998, now abandoned.

(51) Int. Cl.
*A61N 1/365* (2006.01)

(52) U.S. Cl.
USPC .............................................................. 607/9

(58) Field of Classification Search ................. 600/483, 600/509, 526, 528, 545; 607/5, 9–11, 17, 607/67, 88
See application file for complete search history.

(56) References Cited

U.S. PATENT DOCUMENTS

| | | |
|---|---|---|
| 3,032,029 A | 5/1962 | Cunningham |
| 3,762,396 A | 10/1973 | Ballentine et al. |
| 3,773,049 A | 11/1973 | Rabichev et al. |
| 3,837,331 A | 9/1974 | Ross |
| 3,900,034 A | 8/1975 | Katz et al. |
| 3,967,616 A | 7/1976 | Ross |
| 3,989,051 A | 11/1976 | Nozhnikov et al. |
| 4,126,128 A | 11/1978 | Takahashi |
| 4,195,626 A | 4/1980 | Schweizer |
| 4,203,452 A | 5/1980 | Cohen |
| 4,232,678 A | 11/1980 | Skovajsa |
| 4,289,121 A | 9/1981 | Kupriyanovich |
| 4,315,502 A | 2/1982 | Gorges |

(Continued)

FOREIGN PATENT DOCUMENTS

| | | |
|---|---|---|
| EP | 1 024 327 A1 | 8/2000 |
| IL | 77207/2 | 11/1990 |

(Continued)

OTHER PUBLICATIONS

Shin, Shaw-Jyn et al. "Assessment of Autonomic Regulation of Heart Rate Variability by the Method of Complex Demodulation" IEEE Transactions on Biomedical Engineering, vol. 36, No. 2, pp. 274-283 (Feb. 1989).*

(Continued)

*Primary Examiner* — Christopher D Koharski
*Assistant Examiner* — Frances Oropeza
(74) *Attorney, Agent, or Firm* — Sterne, Kessler, Goldstein & Fox PLLC

(57) ABSTRACT

A method and apparatus for affecting the autonomic nervous system of a subject using stimuli based on separate analysis of the sympathetic and/or parasympathetic branches of the subject's autonomic nervous system. The present invention also relates to a method and apparatus for affecting the autonomic nervous system, wherein stimuli is applied in coordination with cyclical activities of the subjects body such as respiration or cardiac cycle.

53 Claims, 8 Drawing Sheets

U.S. PATENT DOCUMENTS

| | | | |
|---|---|---|---|
| 4,436,097 A | 3/1984 | Cunningham | |
| 4,503,863 A | 3/1985 | Katims | |
| 4,508,105 A | 4/1985 | Whitten et al. | |
| 4,510,944 A | 4/1985 | Porges | |
| 4,573,449 A | 3/1986 | Warnke | |
| 4,616,659 A | 10/1986 | Prezas et al. | |
| 4,762,131 A | 8/1988 | Okuda | |
| 4,765,337 A | 8/1988 | Schonberg | |
| 4,777,960 A | 10/1988 | Berger et al. | |
| 4,794,934 A | 1/1989 | Motoyama et al. | |
| 4,832,038 A * | 5/1989 | Arai et al. | 600/483 |
| 4,834,701 A | 5/1989 | Masaki | |
| 4,858,609 A | 8/1989 | Cole | |
| 4,862,361 A | 8/1989 | Gordon et al. | |
| 4,882,535 A | 11/1989 | Gavish | |
| 4,883,067 A | 11/1989 | Knispel et al. | |
| 4,892,106 A | 1/1990 | Gleeson, III | |
| 4,895,149 A | 1/1990 | Morez | |
| 4,896,675 A * | 1/1990 | Ohsuga et al. | 600/484 |
| 4,902,274 A | 2/1990 | Gleeson, III | |
| 4,930,504 A | 6/1990 | Diamantopoulos et al. | |
| 4,966,164 A | 10/1990 | Colsen et al. | |
| 5,036,858 A | 8/1991 | Carter et al. | |
| 5,046,494 A | 9/1991 | Searfoss et al. | |
| 5,047,006 A | 9/1991 | Brandston et al. | |
| 5,076,281 A | 12/1991 | Gavish | |
| 5,079,682 A | 1/1992 | Roberts | |
| 5,108,361 A | 4/1992 | Hein | |
| 5,135,468 A | 8/1992 | Meissner | |
| 5,137,018 A | 8/1992 | Chuprikov et al. | |
| 5,163,426 A | 11/1992 | Czeisler et al. | |
| 5,167,228 A | 12/1992 | Czeisler et al. | |
| 5,176,133 A | 1/1993 | Czeisler et al. | |
| 5,197,941 A | 3/1993 | Whitaker | |
| 5,203,326 A | 4/1993 | Collins | |
| 5,219,322 A | 6/1993 | Weathers | |
| 5,241,967 A | 9/1993 | Yasushi et al. | |
| 5,242,376 A | 9/1993 | Shealy et al. | |
| 5,265,598 A | 11/1993 | Searfoss et al. | |
| 5,291,400 A | 3/1994 | Gilham | |
| 5,292,345 A | 3/1994 | Gerardo | |
| 5,295,491 A | 3/1994 | Gevins | |
| 5,304,212 A | 4/1994 | Czeisler et al. | |
| 5,419,338 A | 5/1995 | Sarma et al. | |
| 5,423,325 A | 6/1995 | Burton | |
| 5,423,328 A | 6/1995 | Gavish | |
| 5,447,527 A | 9/1995 | Waldman | |
| 5,447,528 A | 9/1995 | Gerardo | |
| 5,465,729 A | 11/1995 | Bittman et al. | |
| 5,503,159 A | 4/1996 | Burton | |
| 5,503,637 A | 4/1996 | Kyricos et al. | |
| 5,522,854 A * | 6/1996 | Ideker et al. | 607/6 |
| 5,545,192 A | 8/1996 | Czeisler et al. | |
| 5,562,719 A | 10/1996 | Lopez-Claros | |
| 5,577,990 A | 11/1996 | Widjaja et al. | |
| 5,596,993 A | 1/1997 | Oriol et al. | |
| 5,599,274 A | 2/1997 | Widjaja et al. | |
| 5,603,331 A | 2/1997 | Heemels et al. | |
| 5,643,173 A | 7/1997 | Welles | |
| 5,662,117 A | 9/1997 | Bittman | |
| 5,682,901 A | 11/1997 | Kamen | |
| 5,694,939 A | 12/1997 | Cowings | |
| 5,700,282 A | 12/1997 | Zabara | |
| 5,709,645 A | 1/1998 | Siever | |
| 5,718,235 A | 2/1998 | Golosarsky et al. | |
| 5,727,556 A | 3/1998 | Weth et al. | |
| 5,797,840 A | 8/1998 | Akselrod et al. | |
| 5,800,481 A | 9/1998 | Loos | |
| 5,913,876 A | 6/1999 | Taylor et al. | |
| 5,919,217 A | 7/1999 | Hughes | |
| 5,974,262 A | 10/1999 | Fuller et al. | |
| 6,007,569 A | 12/1999 | Frenkel et al. | |
| 6,017,302 A | 1/2000 | Loos | |
| 6,035,233 A | 3/2000 | Schroeppel et al. | |
| 6,063,108 A | 5/2000 | Salansky et al. | |
| 6,129,748 A | 10/2000 | Kamei | |
| 6,238,424 B1 | 5/2001 | Thiberg | |
| 6,238,425 B1 | 5/2001 | Thiberg | |
| 6,662,032 B1 | 12/2003 | Gavish et al. | |

FOREIGN PATENT DOCUMENTS

| | | |
|---|---|---|
| IL | 86582/2 | 1/1993 |
| IL | 104453/2 | 6/1998 |
| JP | 2000-70373 | 3/2000 |

OTHER PUBLICATIONS

Aguado, L.I. and Ojeda, S.R., "Prepubertal Ovarian Function is Finely Regulated by Direct Andrenergic Influences. Role of Noradrenergic Innervation," *Endocrinology*, vol. 114, No. 5, The Endocrine Society, pp. 1845-1853 (1984).

Akselrod, S. et al., "Power Spectrum Analysis of Heart Rate Fluctuation: A Quantitative Probe of Beat-to-Beat Cardiovascular Control," *Science*, vol. 213, AAAS, pp. 220-222 (Jul. 10, 1981).

Asherman, Joseph G., M.D., "Etiology of Ectopic Pregnancy: A New Concept," *Obstetrics and Gynecology*, vol. 6, No. 6, pp. 619-624 (Dec. 1955).

Ashworth, B., "The Pupil," Quarterly Journal of Medicine, New Series 64, No. 243, Oxford University Press, pp. 549-555 (Jul. 1987).

Bahr, J. et al., "The Role of Catecholamines and Nerves in Ovulation," Biology of Reproduction, The Society for the Study of Reproduction, pp. 273-290 (1974).

Baselli, G. et al., "Autoregressive Modeling and Power Spectral Estimate of R-R Interval Time Series in Arrhythmic Patients," Computers and Biomedical Research, Academic Press, Inc., pp. 510-530 (1985).

Baselli, G. et al., "Heart Rate Variability Signal Processing: A Quantitative Approach as an Aid to Diagnosis in Cardiovascular Pathologies," Int. J. Bio-Medical Computing, Elsevier Scientific Publishers Ireland Ltd., pp. 51-70 (1987).

Benetos, A. et al., "Norepinephrine Applied in the Paraventricular Hypothalamic Nucleus Stimulates Vasopressin Release," Brain Research, Elsevier Science Publishers B.V. (Biomedical Division), pp. 322-326 (1986).

Bental, E. and Hammond-Tooke, G.D., "Vertigo and Drop Attacks Caused by Acute Transient Monocular Disequilibrium (Halpern's Syndrome)," Journal of Neurology, Springer-Verlag, pp. 59-66 (1979).

Bergmanson, J.P.G., "Neural Control of Intraocular Pressure," American Journal of Optometry & Physiological Optics, vol. 59, No. 1, American Academy of Optometry, pp. 94-98 (Jan. 1982).

Bray, G.A., "Nutrient Balance: New Insights Into Obesity," International Journal of Obesity, vol. 11, Suppl. 3, pp. 83-95 (1987).

Bulloch, K. and Pomerantz, W., "Autonomic Nervous System Innervation of Thymic-Related Lymphoid Tissue in Wildtype and Nude Mice," The Journal of Comparative Neurology, Alan R. Liss, Inc., pp. 57-68 (1984).

Cerutti, S. et al., "Spectral Analysis of the Heart Rate Variability Signal," Heart Rate Variability, Futura Publishing Company, pp. 63-74 (1995).

Cvetnić, S. and Cvetnić, V., "Cardiac symptoms and nasal obstruction," Rhinology, vol. 18, pp. 47-50 (1980).

Donchin, Y. et al., "Cardiac vagal tone predicts outcome in neurosurgical patients," Critical Care Medicine, vol. 20, No. 7, Williams & Wilkins, pp. 942-949 (Jul. 1992).

Fairbanks, D.N.F., "Complications of nasal packing," Otolaryngology—Head and Neck Surgery, vol. 94, No. 3, pp. 412-415 (Mar. 1986).

Frohman, L.A., "CNS Peptides and Glucoregulation," Ann. Rev. Physiol., Annual Reviews, Inc., pp. 95-107 (1983).

Halpern, L., "Studies on the Neurobiological Effect of Colours," Problems of Dynamic Neurology, An International Volume, Studies on the Higher Functions of the Human Nervous System, pp. 399-422 (1963).

Ishii, M. et al., "Autonomic Effects on R-R Variations of the Heart Rate in the Squirrel Monkey: An Indicator of Autonomic Imbalance in Conflict Sickness," American Journal of Otolaryngology, vol. 8, No. 3, pp. 144-148 (May 1987).

James, J.E. A., and Daly, M., "Nasal Reflexes," Proc. roy. Soc. Med., vol. 62, pp. 1287-1293 (Dec. 1969).

Kristal-Boneh, E. et al., "Heart rate variability in health and disease," Scand. J. Work. Envrion. Health, vol. 21, No. 2, Occupational Health & Rehabilitation Institute, pp. 85-95 (1995).

Lathers, C.M. et al., "Synchronization of cardiac autonomic neural discharge with epileptogenic activity: the lockstep phenomenon," Electroencephalography and clinical Neurophysiology, Elsevier Scientific Publishers Ireland, Ltd., pp. 247-259 (1987).

Lichtor, T. et al., "The sympathetic nervous system and atherosclerosis," J. Neurosurg., vol. 67, pp. 906-914 (Dec. 1987).

Livnat, S. et al., "Regulation of the Immune System by Sympathetic Neural Mechanisms," Prog. Neuro-Psychopharmacol. & Biol. Psychiat., vol. 11, Pergamon Journals Ltd., pp. 145-152 (1987).

Lowenstein, O. and Loewenfeld, I.E., "The Pupil," The Eye, vol. III, Academic Press, pp. 255-337 (1969).

Malik, M., and Camm, A.J., "Components of Heart Rate Variability—What They Really Mean and What We Really Measure," The American Journal of Cardiology, vol. 72, pp. 821-822 (Oct. 1, 1993).

Malliani, A. et al., "Power Spectral Analysis of Cardiovascular Variability in Patients at Risk for Sudden Cardiac Death," Journal of Cardiovascular Electrophysiology, vol. 5, No. 3, pp. 274-286 (Mar. 1994).

Morse, D.R. et al., "The Effect of Stress and Meditation on Salivary Protein and Bacteria: A Review and Pilot Study," Journal of Human Stress, pp. 31-39 (Dec. 1982).

Niijima, A. et al., "Effects of Light Stimulation on the Activity of the Autonomic Nerves in Anesthetized Rats," Physiology & Behavior, vol. 54, Pergamon Press Ltd., pp. 555-561 (1993).

Öri, Z. et al., "Heart Rate Variability: Frequency Domain Analysis," Ambulatory Electrocardiography, vol. 10, No. 3, pp. 499-537 (Aug. 1992).

Porges, S.W., "Vagal Tone: A Physiologic Marker of Stress Vulnerability," Pediatrics, vol. 90, No. 3, American Academy of Pediatrics, pp. 498-504 (Sep. 1992).

Riga, I.M., "Le Syndrome Neuro-Reflexe De L'Obstruction Nasale Unilatérale," Revue d'Oto-Neuro-Ophthalmo, 24, pp. 325-335 (1957).

Robertson, R.P. et al., "A Role for Alpha-Adrenergic Receptors in Abnormal Insulin Secretion in Diabetes Mellitus," The Journal of Clinical Investigation, vol. 57, pp. 791-795 (Mar. 1976).

Rogers, M.P. et al., "The Influence of the Psyche and the Brain on Immunity and Disease Susceptibility: A Critical Review," Psychosomatic Medicine, vol. 41, No. 2, The American Psychosomatic Society, Inc., pp. 147-164 (Mar. 1979).

Rompelman, O. et al., "Measurement of heart-rate variability: Part 1—Comparative study of heart-rate variability analysis methods," Medical and Biological Engineering & Computing, pp. 233-239 (May 1977).

Rothe, C.F., "Reflex Control of Veins and Vascular Capacitance," Physiological Reviews, vol. 63, No. 4, The American Physiological Society, pp. 1281-1342 (Oct. 1983).

Sanders, V.M. and Munson, A.E., "Norepinephrine and the Antibody Response," Pharmacological Reviews, vol. 37, No. 3, Williams & Wilkins, pp. 229-248 (1985).

Sandin, B. and Chorot, P., "Changes in Skin, Salivary, and Urinary pH as Indicators of Anxiety Level in Humans," Psychophysiology, vol. 22, No. 2, The Society for Psychophysiological Research, Inc., pp. 226-230 (Mar. 1985).

Shimazu, T., "Central Nervous System Regulation of Liver and Adipose Tissue Metabolism," Diabetologia, Springer-Verlag, pp. 343-356 (1981).

Task Force of the European Society of Cardiology and the North American Society for Pacing and Electrophysiology, "Heart Rate Variability: Standards of Measurement, Physiological Interpretation, and Clinical Use," A.N.E., vol. 1, No. 2, Pt. 1, pp. 151-181 (Apr. 1996).

van Ravenswaaij-Arts, C.M.A. et al., "Heart Rate Variability," Annals of Internal Medicine, vol. 118, No. 6, pp. 436-447 (Mar. 15, 1993).

Vander, Arthur J. et al., Human Physiology, McGraw-Hill Inc. 1970, p. 163.

Weisz, J. et al., "The influence of monocular viewing on heart period variability," International Journal of Psychophysiology, Elsevier Science Publishers B.V., pp. 11-18 (1992).

Wetterberg, L., "Frontiers in Medicine: Light and biological rhythms," Journal of Internal Medicine, pp. 5-19 (1994).

Williams, M.E. et al., "Role of α-adrenergic hormones in potassium homeostasis in the rat," J. Lab. Clin. Med., vol. 110, No. 2, pp. 245-249 (Aug. 1987).

Woo, M.A. et al., "Complex Heart Rate Variability and Serum Norepinephrine Levels in Patients With Advanced Heart Failure," JACC, vol. 23, No. 3, The American College of Cardiology, pp. 565-569 (Mar. 1, 1994).

Patent application serial No. 104,453/2 published Jun. 18, 1996, by Benjamin Gavish entitled: Stress Detecting Device and Method for Monitoring Breathing.

Patent application serial No. 86582/2 publish Jan. 31, 1993, by Benjamin Gavish entitled: Device and Method for Modulating Respiration Activity.

Patent application serial No. 77202/2 published 1990 by Benjamin Gavish entitled: A Device and Method for Monitoring Small Displacements of a Peak in a Frequency Spectrum.

English Abstract for JP 2000-70373, 1 page, from the espacenet database, Mar. 7, 2000.

* cited by examiner

|  AMPLITUDE | DIRECTION |
|---|---|
| $\frac{\Delta S}{S}$ | $D(s)$ |
| $\frac{\Delta A}{A}$ | $D(a)$ |
| $\frac{\Delta A}{A}$ | $D(a)$ |
| $\frac{\Delta S}{S}$ | $D(s)$ |

COLOR HUE
COLOR BRIGHTNESS
SOUND FREQUENCY
SOUND LOUDNESS

FIG.8

METHOD AND APPARATUS FOR AFFECTING THE AUTONOMIC NERVOUS SYSTEM

The present application is a continuation of U.S. application Ser. No. 10/778,306, filed Feb. 17, 2004, now abandoned, which is a continuation of U.S. application Ser. No. 09/715,046, filed on Nov. 20, 2000, which is abandoned, which is a continuation of U.S. application Ser. No. 09/176,566, filed on Oct. 21, 1998, which is abandoned.

BACKGROUND OF THE INVENTION

1. Field of Invention

The present invention relates generally to a method and apparatus for affecting a subject's health or condition by using information regarding the sympathetic and/or parasympathetic branches of the subject's autonomic nervous system to apply and/or modulate stimuli to the subject. The present invention also relates to a method and apparatus for affecting the autonomic nervous system, wherein stimuli is applied in coordination with cyclical activities of the subject's body.

2. Background Art

The autonomic nervous system (ANS) and its role in health and pathology is a field of medicine that has been explored and written about at great length. There are also several prior art methods and devices that use the concept of applying sensory stimuli to a subject's body to affect the subject's health or condition.

I. Application of Stimuli to Affect the Body

The prior art includes methods and devices for applying stimuli to a patient's body. For example, U.S. Pat. No. 5,577,990 to Widjaja et al. discloses a device that directs light and sound toward a patient, apparently eliciting a relaxation response from the patient. It is also known in the art to combine stimuli with feedback from the body. For example, U.S. Pat. No. 5,562,719 to Lopez-Claros discloses a method and apparatus for treating disorders such as Seasonal Affective Disorder by preferentially directing light therapy to the non-dominant hemisphere of the brain. In addition, U.S. Pat. No. 4,289,121 to Kupriyanovich discloses a method and device for controlling the functional state of the central nervous system using audio and light signals applied according to the body's biorhythms that correspond to a stable state of the central nervous system. This reference describes modulating frequencies depending on the electroencephalogram (EEG), electrocardiogram (ECG), or the measured respiration rate of the patient, wherein the amplitude or rhythmic signals correspond to the volume of sound and brightness of light. Kupriyanovich also suggests that the device include a feedback system to automatically vary the illumination in response to certain changes in the patient's vital signs, including the patient's pulse rate, temperature, and respiratory rate. A patient's vital signs, however, do not provide complete information about the autonomic nervous system. The same vital sign reading for one patient may represent different levels of sympathetic and parasympathetic activity. Therefore, the complexity or the various dimensions of the autonomic nervous system activity is not fully reflected in a patient's vital sign measurements or in the patient's biorhythms.

In addition, in the prior art methods and devices, stimuli which generally affect the sympathetic branch differently than the parasympathetic branch, are applied without regard to the autonomic nervous system balance and activity. For example, U.S. Pat. No. 5,076,281 to Gavish discloses a biorhythm modulator, which produces music-like sound pattern signals based on a patient's biorhythmic activity. Although Gavish notes that certain activities of the body are associated with the sympathetic nervous system, the rhythm of the sound synthesized patterns are based simply on a patient's monitored respiration rate, and not on separate analyses of the sympathetic and parasympathetic branches of the autonomic nervous system.

The prior art also includes stimulation treatments and biofeedback treatments that involve the patient's cognitive awareness and involvement in the treatment. These treatments are also known to include adjustment of the stimuli through trial and error. In the Kupriyanovich reference described above, the patient chooses the initial light and audio signals. However, a patient's subjective feelings do not accurately reflect the complex interactions of the patient's autonomic nervous system.

It is known that, generally, colors ranging from green to blue or violet are calming colors, and that these colors have the effect of stimulating the parasympathetic branch. It is also known that, generally, colors ranging from red to yellow are rousing colors, and that these colors have the effect of stimulating the sympathetic branch. Hospitals tend to incorporate greens and blues in their interior color scheme in order to calm and soothe patients, whereas fast food restaurants are typically red, yellow, and orange in order to move customers in and out of the restaurants quickly. In addition, it is known that increasing the brightness or intensity of a color increases its stimulatory effect.

It is also known that, generally, sounds having a pitch below 500 cycles or Hz tend to have a calming effect, whereas sounds having a pitch above 500 cycles tend to have a rousing effect. In addition, it is known that the louder the sound, the greater the stimulation.

As is apparent from the discussion above, known methods or devices generally do not provide for treatment of a patient based on the full range of information which can be ascertained from the condition of the autonomic nervous system. For example, prior art treatment methods or devices generally do not take advantage of independent or separate analyses of the sympathetic and parasympathetic branches of the autonomic nervous system.

II. The Autonomic Nervous System and Heart Rate Variability

A. Nervous System

The nervous system comprises the central nervous system and the peripheral nervous system. The central nervous system comprises the brain and spinal cord, and the peripheral nervous system comprises a network of nerves that connects the brain and spinal cord to the rest of the body.

The brain, which is the site of cognitive awareness and the control center for the rest of the body, comprises the cerebrum, the brain stem, and the cerebellum. The brain coordinates the ability to move, touch, taste, smell, hear, and see. The cerebrum regulates a variety of voluntary activities of the body, including speech, thought, planning, and initiating communication or action.

A variety of critical body functions are automatically regulated by the brain stein. These functions include adjusting posture, regulating breathing, swallowing, and heart rate, controlling the rate at which the body burns food, and increasing alertness when needed. The autonomic nervous system is a part of the peripheral nervous system and comprises the nerves that communicate between the brain stem and the body's internal organs.

The autonomic nervous system comprises the sympathetic and parasympathetic branches or systems, and it functions below the conscious level through complex interactions between its two branches to respond quickly and continuously to perturbations that threaten the stability of the body's internal environment.

Responses to sympathetic and parasympathetic stimulation are frequently antagonistic. For example, they have opposing or antagonistic effects on heart rate. Whereas stimulation of the sympathetic branch increases heart rate, stimulation of the parasympathetic branch decreases heart rate. In addition, the body's response to activity in one branch depends on the level of activity in the other branch.

A useful, albeit simplistic, analogy for the parasympathetic and sympathetic branches is that the sympathetic branch functions as the body's gas pedal and the parasympathetic branch functions as the body's brakes. Sympathetic and parasympathetic activity make up a complex, dynamic system that is continuously adjusting to changing conditions in the body and in the outside environment. The autonomic nervous system strives to optimize activity in each branch and to balance the two branches at every passing moment, depending on both internal and external conditions.

B. Heart Rate

Normal rhythmic contractions of the heart occur because of spontaneous electrical pacemaker activity of cells in the sinoatrial (SA) node. The heart rate, i.e., the time interval between heartbeats, is determined by how long it takes the membranes of these pacemaker cells to spontaneously depolarize to the threshold level. The heart beats at a spontaneous or intrinsic rate, which is approximately 100 beats per minute, in the absence of outside influences. Outside influences are required to increase or decrease the heart rate from its intrinsic rate.

The two most important outside influences on heart rate come from the autonomic nervous system. Fibers from both the sympathetic branch and parasympathetic branch of the autonomic nervous system terminate on cells in the SA node and both can modify the intrinsic heart rate. Activating the cardiac sympathetic nerves increases cardiac sympathetic tone, thereby increasing heart rate. Increasing cardiac parasympathetic tone, on the other hand, slows the heart rate. Both sympathetic and parasympathetic nerves influence heart rate by altering the course of spontaneous depolarization of the resting potential in SA pacemaker cells.

C. Heart Rate Variability (HRV)

Heart rate variability is the amount of heart rate fluctuation around a mean heart rate. Such fluctuations reflect oscillations in sympathetic-parasympathetic balance associated with a variety of factors, including respiration, baroreceptor reflexes, vasomotor control, and thermoregulatory processes. The main periodic fluctuations found are respiratory sinus arrhythmia and baroreflex-related and thermoregulation-related heart rate variability.

Heart rate variability is demonstrated by every normal person's heart, regardless of that person's state of health and regardless of the presence of stress or disturbances. Even a sleeping person displays heart rate variability. Each person has a measurable baseline heart rate variability even in the absence of external stressors, such as traffic, screaming babies, and looming deadlines.

Heart rate variability can be used as a mirror of the cardiorespiratory control system, and it is a valuable tool to investigate the sympathetic and parasympathetic function of the autonomic nervous system. Heart rate variability provides information about sympathetic-parasympathetic interplay and balance, which includes other valuable information about the nervous system, including, for example, the risk for sudden cardiac death in patients after myocardial infarction.

Heart rate variability measurements are easy to perform, are noninvasive, and are easily and accurately reproducible. In addition, heart rate variability has been found to be largely unaffected by placebos.

Heart rate variability can be influenced by physiologic and maturational factors. Maturation of the autonomic nervous system results in an increase in heart rate variability with gestational age and during early post-natal life. Heart rate variability decreases with age, and this decline begins in childhood. In addition, heart rate variability is influenced by provocation and physical disorders.

SUMMARY OF THE INVENTION

The present invention relates generally to a method and apparatus for affecting a subject's health or condition by using information regarding the sympathetic and/or parasympathetic branch of the autonomic nervous system to modulate and/or apply stimuli to the patient. This invention may be used to treat patients with various pathologies as well as to treat healthy subjects in order to improve or refine the functioning of their autonomic nervous system.

One aspect of the present invention involves stimulation of the autonomic nervous system based on separate analysis of the sympathetic branch and/or the parasympathetic branch of the autonomic nervous system. In a preferred embodiment, this invention does not require any physical or mental efforts on the part of the patient, nor does it involve the patient's cognitive awareness or involvement. The present invention may even be used to treat a sleeping patient. In a preferred embodiment the autonomic nervous system is monitored and the stimuli is modulated by continuous assessment of heart rate variability.

Another aspect of the present invention is to provide a real-time feedback loop or system, wherein information about the autonomic nervous system is continuously monitored and then fed back or conveyed to the patient through afferent neural pathways, i.e., nerves that conduct impulses from the periphery of the body inward to the spinal cord. In a preferred embodiment, this feedback loop is carried out by application of sensory stimuli.

Another aspect of the present invention is to coordinate the stimuli with specific phases of cyclical activities of the body, such as systole or diastole in the cardiac cycle, and inspiration or expiration in the breathing cycle.

BRIEF DESCRIPTION OF THE FIGURES

Reference is next made to a brief description of the figures, which are intended to illustrate the apparatus and method according to the present invention. The figures and detailed description which follow are intended to be merely illustrative, and are not intended to limit the scope of the invention as set forth in the appended claims.

FIG. 8 is a chart summarizing the stimuli parameters in one embodiment of the present invention as shown in FIG. 4.

DETAILED DESCRIPTION OF THE INVENTION

The present invention is generally directed toward affecting a patient's autonomic nervous system, whether to treat a condition or simply to enhance performance of the autonomic nervous system. In a preferred embodiment the invention involves applying one or more default sensory stimuli, such as a visual stimulus and/or an audio stimulus to the patient, obtaining separate information about the parasympathetic and/or sympathetic branches of the autonomic nervous system by monitoring the patient, which information is preferably used to continuously alter the default stimuli according to the information obtained. In a preferred method, information about the autonomic nervous system is obtained by transforming the patient's ECG electrical signal into a measurement of heart rate variability parameters as a function of frequency.

Figure 1:
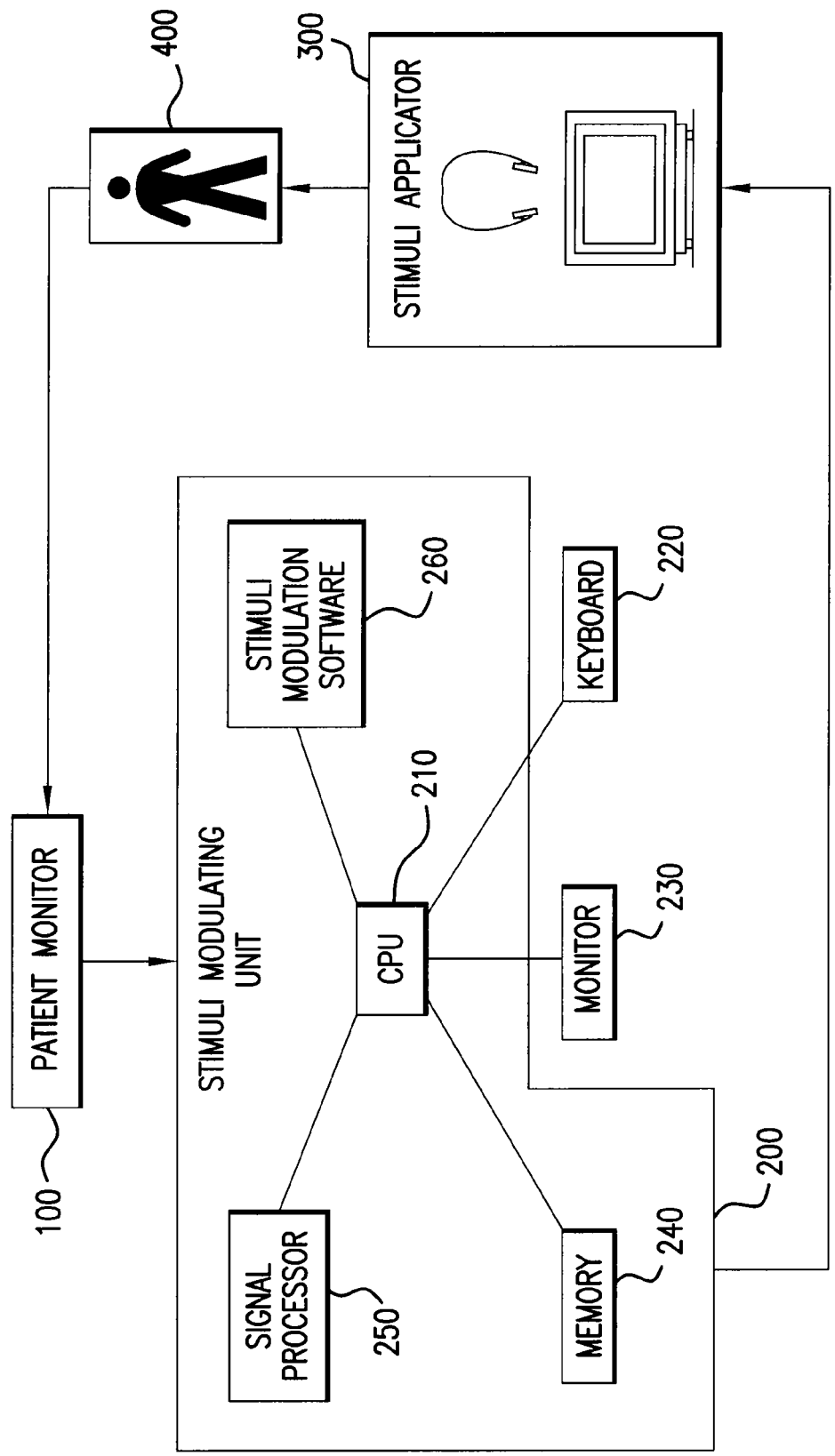
FIG. 1 is a block diagram, generally illustrating an embodiment of an apparatus of the present invention.

An apparatus according to one embodiment of the present invention is depicted schematically in FIG. 1. As shown in this figure, the apparatus generally comprises patient monitor 100, stimuli modulating unit 200, and stimuli applicator 300.

Patient or subject monitor 100 is utilized to monitor a condition of the patient or subject that may be analyzed to separately assess sympathetic and/or parasympathetic activity of the patient's autonomic nervous system. The monitored patient condition or parameter may be any patient activity, including physiological, cognitive, and behavioral activity of the patient or subject. In a preferred embodiment, patient monitor 100 comprises commercially available ECG machine. Other suitable patient monitors include digital cameras to quantify the amount of the body's agitation, and a skin resistance galvanometer.

Signals representative of the patient condition monitored are transmitted to stimuli modulating unit 200 by patient monitor 100. The apparatus is controlled by stimuli modulating unit 200, which includes central processing unit (CPU) 210, memory 240, in which data may be stored, signal processor 250, and stimuli modulation software 260, which contains the expert system comprising the algorithm to control the stimulus or stimuli. In a preferred embodiment, CPU 210 is coupled with monitor 230 and/or keyboard 220 to provide an interface with the operator of the apparatus. However, these interface elements are optional and may comprise alternative elements known in the art. Several of these components (i.e., CPU 210, keyboard 220, monitor 230, memory 240, signal processor 250) are well known in the art. In fact, these components are included in most existing computers.

In an exemplary embodiment, the apparatus includes an electrocardiograph connected to a standard Intel based personal computer (PC) or workstation with a color monitor, a soundboard, and an audio headset. The electrocardiograph is used to measure electrical currents associated with heart muscle activity, from which the subject's HRV may be analyzed and the subject's sympathetic and/or parasympathetic activity assessed. The algorithm is executed by the PC, the visual output is displayed on the color monitor, and the audio output is transmitted by the headset.

Figure 6:
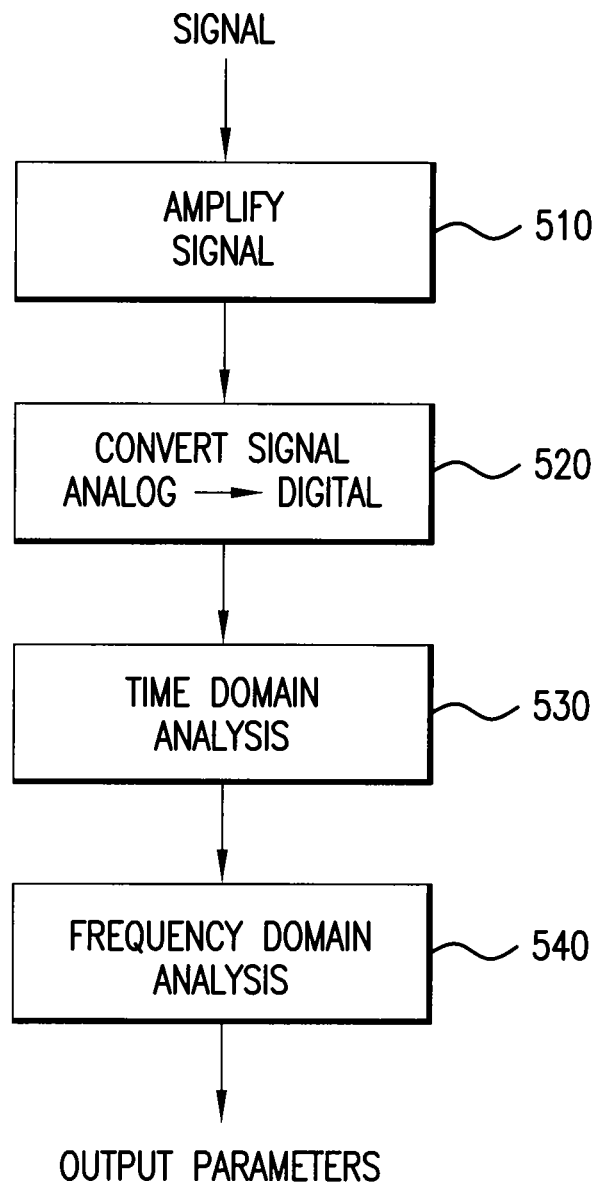
FIG. 6 is a flowchart depicting the function of the signal processor in one embodiment of the present invention.

The functions performed by signal processor 250 are shown in the flowchart of FIG. 6. First, as indicated in step 510, signal processor 250 amplifies the signal received from patient monitor 100. Then, in step 520, the analog signal is converted to a digital signal. It should be noted that some of the steps shown in FIG. 6 may not be required. For example, if the signals received by signal processor 250 are digital signals, then converting the signal to a digital signal, i.e., step 520, is obviously not necessary. Next, in step 530, a time domain analysis is performed on the signal. This is followed by step 540 comprising a frequency domain analysis of the signal. The hardware necessary to perform these functions are well known in the art. Alternatively the functionality of signal processor 250 may be incorporated in software as part of stimuli modulation software 260 or separately in memory 240, as is known in the art. Ultimately, signal processor 250 produces output parameters which are indicative of sympathetic and/or parasympathetic activities of patient 400.

Figure 7:
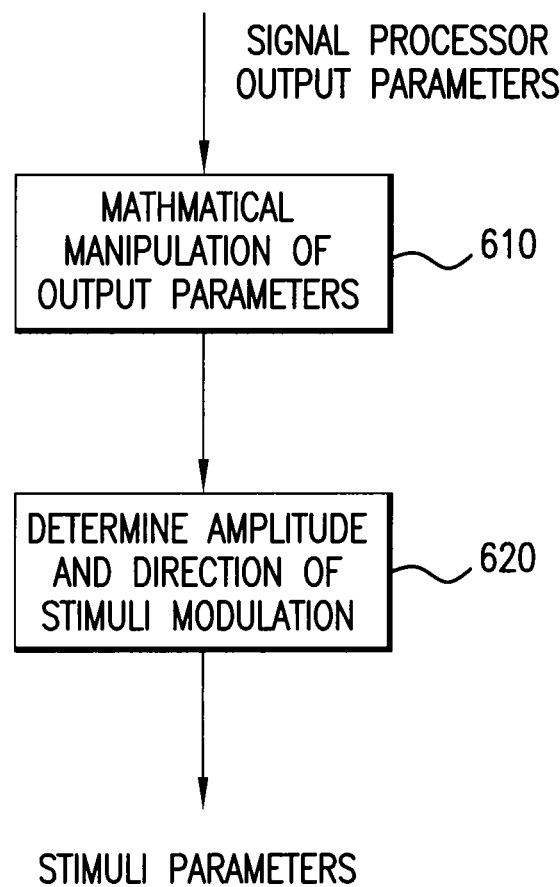
FIG. 7 is a flowchart depicting the function of the stimuli modulation software in one embodiment of the present invention.

The stimulation modulation software 260 then determines the appropriate stimuli or the appropriate modulation of the stimuli. The algorithm by which this is accomplished is depicted in the flowchart of FIG. 7, and is described in detail herein.

Stimuli applicator 300 applies appropriate stimulus to the patient 400 based on information received from modulating unit 200. As schematically represented in FIG. 1, applicator 300 may include headphones for sound stimulus and a television or computer monitor for light stimulus. Light stimuli may be applied in any suitable manner, such as by LCD or CRT monitor, incandescent, fluorescent, or neon lighting. A variety of different types of stimuli also may be used, including pressure applied to the patient and thermal radiation. Also, virtual reality helmets may be used as applicator 300, including an open or closed helmet with glasses and earphones attached. The apparatus may be completely wireless, incorporating infrared technology.

According to further alternative embodiments of the present invention, it is not necessary that all components of the apparatus be located together or directly linked together. For example, a subject provided with ECG electrodes and an appropriate interface to his or her own home computer could access modulating unit 200 or both patient monitor 100 and modulating unit 200 at a remote location via the Internet or a direct dial-in connection. The multimedia features of current home computers make them ideal stimuli applicators 300, providing both sound and light stimuli. Alternatively, patient monitor 100 and stimuli applicator 300 may be incorporated together into a home unit which would communicate with modulating unit 200 via a standard telephone connection. In this embodiment, subjects without home computers or computer skills would simply dial in to the care provider for treatment without having to make regular visits to a clinic or other treatment center. Regular, periodic dial-in sessions would create individual patient histories which may be automatically monitored for significant variations to provide automatic warnings to appropriate caregivers as may be required. In alternative embodiments, signal processor 250 and stimuli modulation software 260 may be downloaded from the Internet to home computers, such as personal computers, Web TVs, and Digital TVs.

According to the method of the present invention, the patient is monitored in order to ascertain the activity of the sympathetic and/or parasympathetic branch of the patient's autonomic nervous system. In the preferred embodiment, this activity is assessed through analysis of the patient's heart rate variability (HRV). Measuring heart rate variability, as opposed to simply heart rate, yields a wealth of information about the autonomic nervous system which leads to improved diagnosis of a variety of pathologies, including hypertension, cardiac ischemia, myocardial infarction, diabetic neuropathy and other autonomic dysfunctions. Improved diagnosis in turn leads to more specific, and subsequently more effective, therapy.

The measurement of heart rate variability contains information about several physical parameters of autonomic nervous system activity, including heart rate. Therefore, this measurement provides a multi-dimensional picture of the patient's condition that could not otherwise be obtained from simply measuring a patient's heart rate, which is simply the average number of heartbeats in a certain time interval. Information about the autonomic nervous system provided by heart rate variability as compared to heart rate is analogous to information about a moving body provided by acceleration and velocity measurements as compared to only velocity measurements. Because heart rate variability measurements provide a more complete picture, better diagnosis and treatment may be obtained based on analysis of heart rate variability as opposed to simply heart rate.

It should be noted, however, that any method of monitoring or assessing the activity of the autonomic nervous system, for example breathing, may be incorporated in the present invention as long as sympathetic and/or parasympathetic branch of the autonomic nervous system may be separately analyzed.

Figure 2:
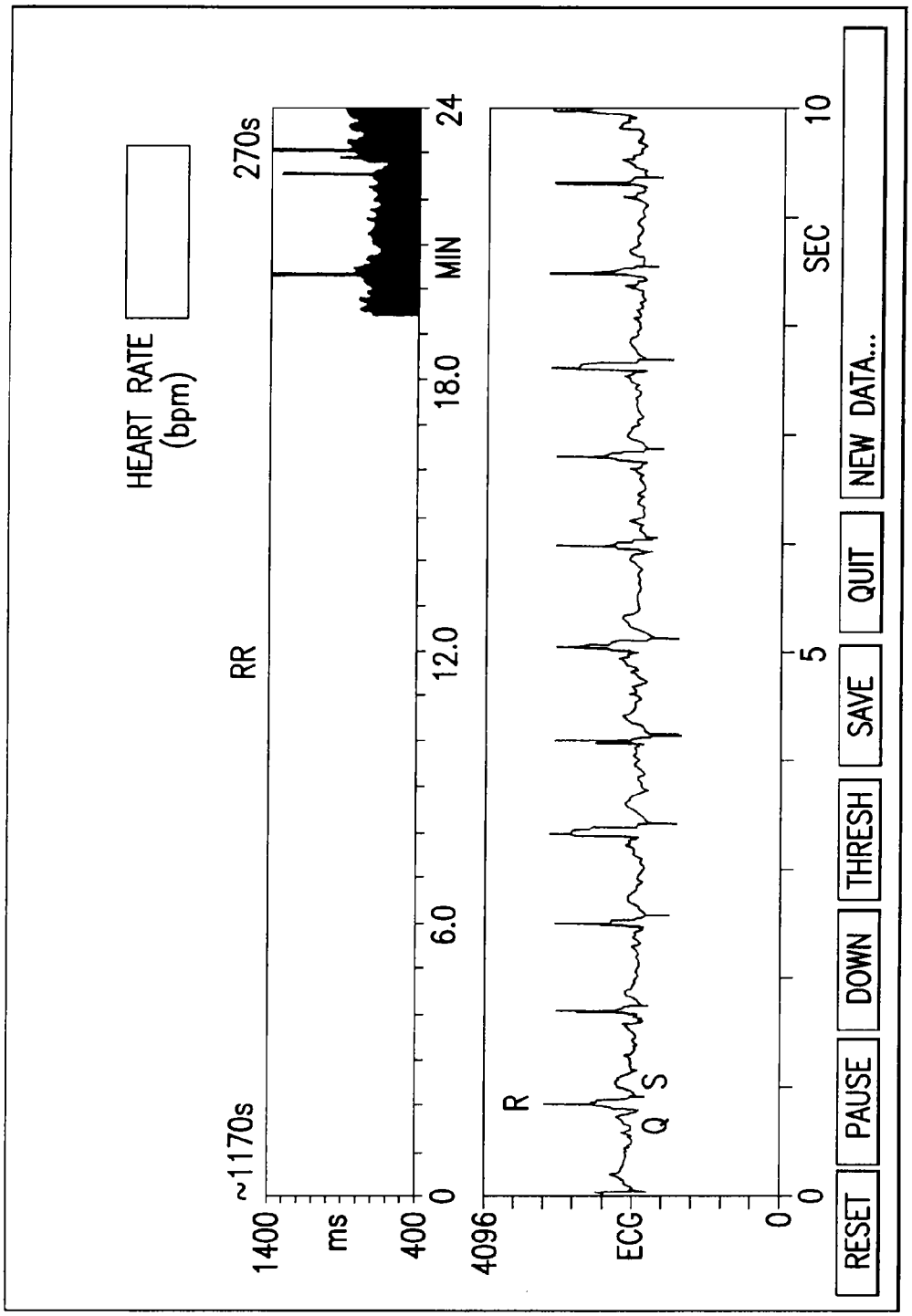
FIG. 2 is an electrocardiogram (ECG) of a typical series of heartbeats, each showing the QRS complex, from which a fiducial point is identified in order to measure heart rate and heart rate variability.

As shown in FIG. 7, in step 610, the signal processor output parameters are mathematically manipulated. According to the preferred method, autonomic nervous system activity is measured through statistical and spectral analysis of a series of RR intervals from a patient's ECG. In this analysis, a resting baseline ECG of the patient is first obtained by a standard electrocardiograph. Such an ECG is illustrated in FIG. 2. As shown in FIG. 2, each heartbeat includes what is referred to as a QRS complex. The average QRS complex spans approximately 75 msec.

Errors, resulting from noise effects, missing data, arrhythmic or ectopic beats will distort the HRV analysis. These errors may be eliminated or reduced through interpolation of previous or successive RR intervals in the ECG signal. Other algorithms known in the art such as linear regression or autocorrelation functions may also be used to reduce these errors.

To obtain an HRV measurement with minimal noise, the subject is instructed not to engage in certain activities for approximately four hours prior to taking the ECG, which may affect his heart rate and heart rate variability, such as taking stimulants, including chocolate. The ECG is taken while the subject is at rest in a semi-supine position. While the heart rate is being monitored, the subject is instructed to keep still and to avoid physical and mental activities such as chewing gum, making mathematical calculations, or memorizing information.

Figure 3:
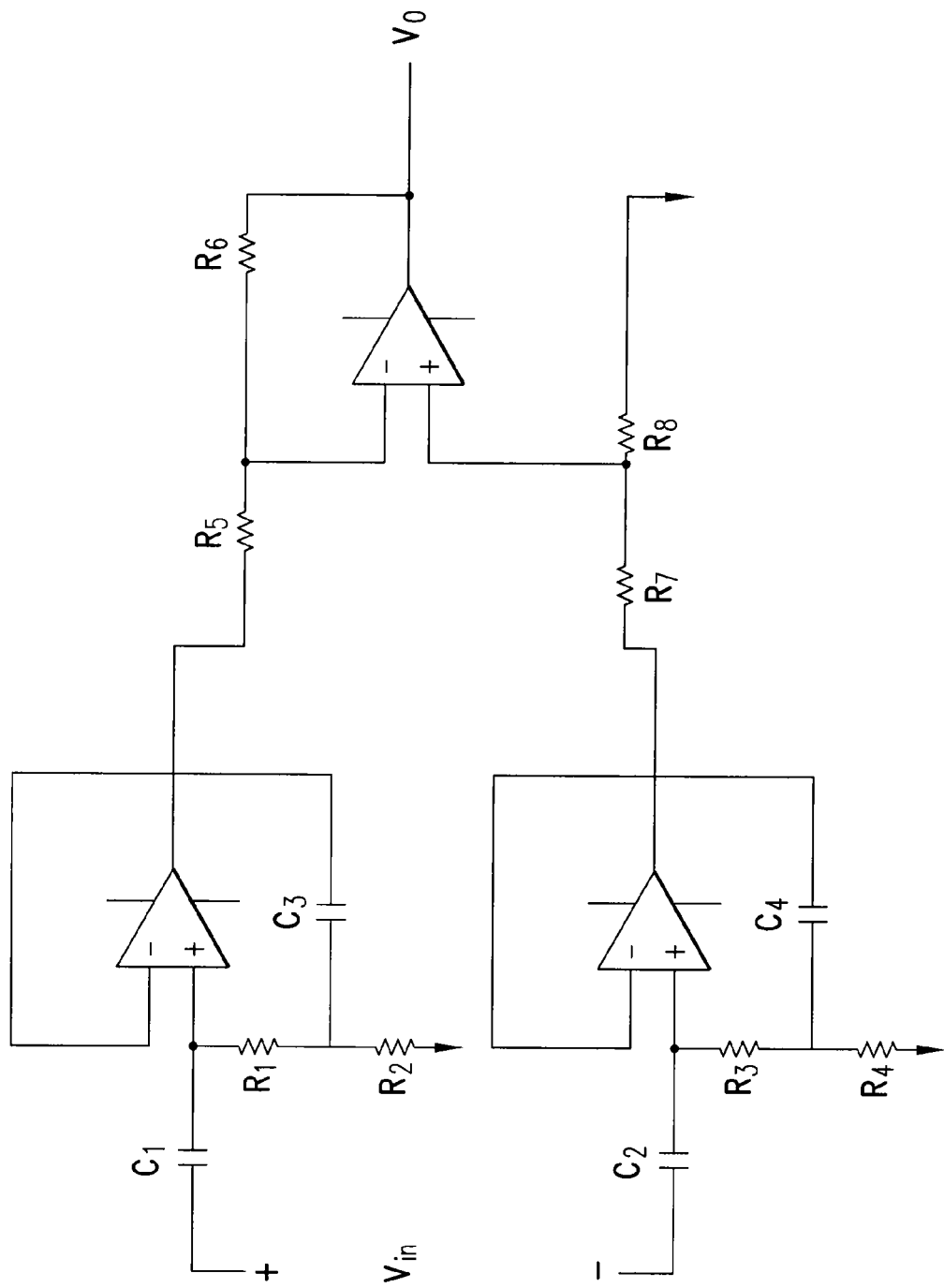
FIG. 3 is a schematic of an amplifier, which may be used in the apparatus of the present invention.
Figure 4:
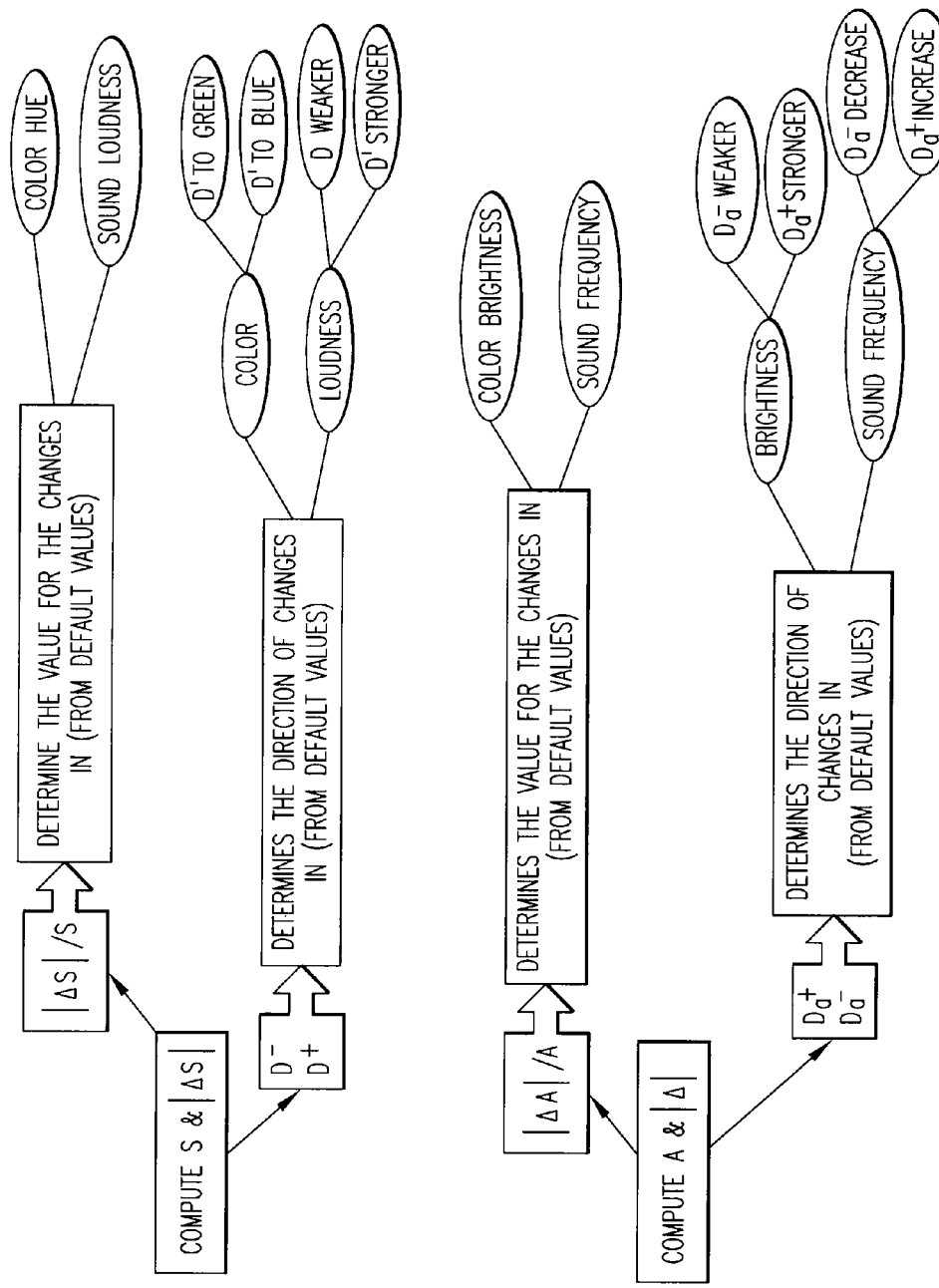
FIG. 4 is a block diagram, generally illustrating an embodiment of the method of the present invention.

The ECG signal, which is in the millivolt range, is then amplified into the volt range (see step 510 in FIG. 6). Several amplification methods are known in the art. Typically, amplifiers are manufactured to order, and special hardware may be designed for this particular application. A type of ECG amplifier schematic that is appropriate for the present invention is shown in FIG. 3. This circuit diagram employs known symbols for circuit elements. This ECG amplifier has two input bootstrapped buffers as an input stage and a differential amplifier as an output stage. The bootstrapped buffer makes the input impedance very high both at d.c, and at 50 Hz. The total gain for this amplifier is 180, One of ordinary skill will be able to construct an amplifier based on this circuit diagram or an appropriate amplifier for the present invention. Alternatively, one may incorporate already existing software or any other suitable amplification method known in the art.

The analog signal is then sampled and transformed into a digital signal by a standard digital signal processing card preferably having 12-bit resolution (see step 520 in FIG. 6). The electrocardiograph itself may be provided with a digital output. For the present method, it is sufficient to sample the ECG signal at a rate of 1000 times per second. Obviously, however, sampling at a higher rate up until the Nyquist rate will improve the accuracy of the digital representation, whereas sampling at a lower rate reduces the signal to noise ratio. In any case, a sampling rate lower than 500 times per second is not recommended.

The digital signal is then processed using the pattern recognition method described herein, or any other suitable mathematical technique known in the art (see step 530 in FIG. 6). The pattern recognition method is preferred because it renders accurate readings even for erratic signal patterns, such as may be obtained, for example, from hyperactive kids. Through more sophisticated pattern recognition methods, increasingly stable and noise independent fiducial points may be obtained based on fewer data points.

According to standard pattern recognition methods known in the art, linear regression is used on the QR slope data and the RS slope data to obtain the most representative straight line for both the QR slope and the RS slope. The point of intersection of both lines represent the $R_n$ fiducial point for each QRS waveform$_n$. The time lag between $R_n$ $R_{n+1}$ and is the value RR, which is typically expressed in milliseconds, and a series of RR values is referred to as an RR series.

The RR values resulting from sinoatrial (SA) node depolarization are referred to as normal to normal (NN) intervals, and in the present invention, only the NN values are considered. The method of transforming an RR series into an NN series is well known in the art.

A series of NN values are measured over a segment or time window defined by N heartbeats, and the heart rate variability parameters of interest are calculated based on the ECG recording within the segment, where N=30 k and k is an integer between 1 and 6, and 4 and 120 are the default values for k and N respectively. This process is repeated continuously until the end of the treatment over successive segments or time windows, wherein the starting points of each time window are separated by a predetermined interval. In the preferred embodiment, this predetermined interval is determined by M heartbeats. The preferred values for M are 4, 10, and 23, and 4 is the default value for M.

Typically, the subject's ECG is obtained both to measure the subject's baseline HRV and to monitor the subject during treatment. The type of stimuli to be used and the parameters of the stimuli to be modulated is initially determined based on evaluation of the patient's baseline HRV. This baseline HRV may be obtained from a single ECG segment of at least 1500 RR intervals, which typically will require no more than 24 minutes of recording. During treatment, on the other hand, the subject's ECG is continuously obtained until the end of the treatment, wherein several successive segments of heartbeats are identified, and wherein each segment comprises N heartbeats, as explained above. Stimuli is applied and modulated based on information about the autonomic nervous system obtained from these segments.

Heart rate variability may be determined in at least the following two ways: (1) by calculation of indices based on statistical operations on NN intervals (time domain analysis) or (2) by spectral (frequency domain) analysis of an array of NN intervals.

To assess baseline values of HRV or to calculate changes in ANS activity during treatment, the following time domain parameters of HRV may be used in the present method:
1. mean NN intervals (mNN);
2. mean heart rate as derived from the mean NN intervals;

3. difference between the minimal and maximal NN interval;
4. standard deviations of the NN intervals (SDNN), which is the root of variance;
5. root mean square of successive differences in the NN intervals (rMSSD); and
6. percentile of intervals in which the absolute value of the difference between them is greater than 50 msec (Pnn50).

In alternative embodiments of the present invention, these parameters and other time domain parameters of ANS activity can provide information to apply or modulate sensory stimuli to the patient.

Frequency domain analysis or power spectral density (PSD) analysis is a preferred method for measuring heart rate variability according to the present invention (see step 540 in FIG. 6). This analysis provides a measurement of power as a function of frequency. PSD analysis enables one to evaluate the contribution to variance of frequency-specific oscillations. Therefore, one can measure not only the amount of variability, but also its distribution in relation to oscillation frequency (i.e., number of heart rate or NN value fluctuations per second). The point of PSD analysis is to pass from a continuous time function, i.e., the ECG tracing or curve, to a discrete-time function, which is representative of the instantaneous heart rate.

There are a number of methods of performing frequency domain analysis. Two popular methods include fast Fourier transformation and autoregressive (AR) modeling. Both methods are well known in the art, and both yield similar results. Fast Fourier transformation spectra, however, are characterized by discrete peaks for the several frequency components, whereas the autoregressive method results in continuous smooth spectra of activity. Fast Fourier transformation analysis is particularly useful in determining the area under the spectrum, whereas AR modeling is particularly useful in determining central tendencies or peaks in given frequency ranges.

Other methods of performing frequency domain analysis includes coarse-graining spectral analysis, useful in extracting the harmonic components from a broad band noise spectrum and wavelet analysis, capable of processing data at different scales or resolutions, a method well suited for approximating data containing sharp discontinuities.

Fourier analysis is a simple, widely used technique that involves decomposing the series of sequential RR intervals into a sum of sinusoidal functions of different amplitudes and frequencies. The resulting power spectrum can be graphed as the magnitude of variability as a function of frequency. The power spectrum therefore reflects the amplitude of the heart rate fluctuations present at different oscillation frequencies. Fourier analysis may be performed on a short ECG recordings of 0.5 minute to several minutes to much longer recordings.

The autoregressive model is a linear prediction formula that attempts to predict an output y[n] of a system based on previous outputs (y[n−1], y[n−2], etc.) and inputs (x[n], x[n−1], x[n−2], etc.). Deriving the linear prediction formula involves determining the coefficients a1, a2, and b0, b1, b2, etc. in the following equation:

$$y[n](\text{estimated}) = a1*y[n-1] + a2*y[n-2] \ldots + b0*x[n] + b1*x[n-1] + \ldots$$

In other words, the system is determined by calculating a set of coefficients that yield an accurate prediction y[n]. The model will differ depending on the order of the model (n) chosen, higher orders corresponding to larger n values. Higher order models will produce higher resolution and more noise, whereas lower order models will produce less noise, or a smoother result, comprising less information.

Other than the time and frequency analyses of a series of NN intervals outlined above, geometrical methods can also provide information about HRV. The most common geometrical methods include: a) sample density distribution of NN interval duration; b) sample density distribution of differences between adjacent NN intervals; and; c) Lorenz plot of NN or RR intervals (i.e., XY scattergram). These analyses yield shapes or patterns (e.g., the Lorenz plot characteristically yield linear, triangular, or elliptical shapes). and the geometrical and/or graphical properties of these resulting patterns provide information about various aspects of HRV. Again, any method that provides separate information about the sympathetic and/or parasympathetic branches of the ANS may be incorporated in the present invention.

Periodic variations in heart rate at different frequency ranges reflect different aspects of autonomic nervous system activity. The method of the present invention generally focuses on short-term ECG segments. For these short term segments, the following spectral bands may be identified: a) a very low frequency (VLF) band from 0.003 Hz to 0.04 Hz; b) a low frequency (LF) band from 0.04 Hz to 0.15 Hz; and c) a high frequency (HF) band from 0.15 Hz to 0.45 Hz in adults and to 0.5 Hz in children. Because the VLF band may contain many non-periodic components and may be significantly affected by certain algorithms used in the HRV analysis, it is not considered in a preferred embodiment of the present invention.

Figure 5:
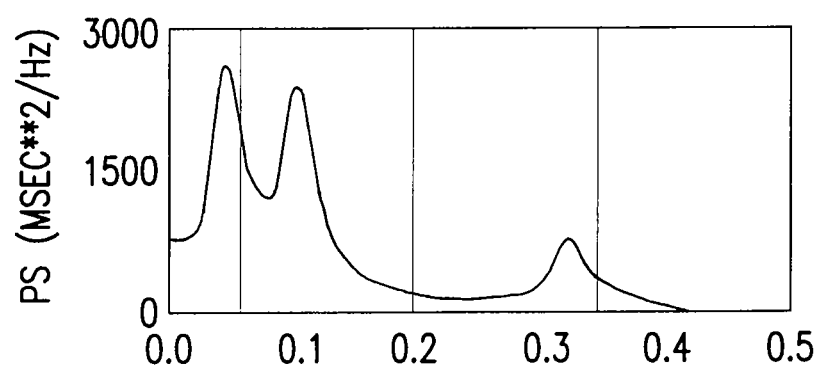
FIG. 5 illustrates a typical power spectrum.

In a preferred embodiment of the present invention, PSD analysis is used to measure heart rate variability. Specifically, the 16th order transformation of the AR model is used. An example of a power spectrum obtained by such an analysis is shown in FIG. 5, depicting a graph of variability (i.e., power) as a function of frequency (Hz).

Variability measurements below 0.15 Hz on the variability curve is generally a reflection of sympathetic activity, and variability measurements above 0.15 Hz is generally a reflection of parasympathetic activity. Separate evaluation of the parasympathetic and sympathetic branches of the ANS is possible through PSD analysis. The power spectrum may also be divided into several other frequency bands or regions, in addition to or other than these two classical frequency regions. For example, the power spectrum above 0.04 Hz may be divided into three regions, wherein the lower region is below approximately 0.08 Hz, the middle region is located between approximately 0.08 Hz and 0.15 Hz, and the high region is above 0.15 Hz.

Characterizing each frequency region are two parameters of particular interest: the area under the curve of the power spectrum (S), which represents variance and is measured in msecz; and the height of the curve at its peak (A), representing the maximum value of variability within the frequency region and is measured in $msec^2/Hz$. The methods of the present invention also includes other parameters which are derived from these parameters, including: (a) absolute value in the change in S over consecutive time windows (|ΔS|); (b) the absolute value in the change in A over consecutive time windows (|ΔA|); (c) the absolute fractional change of S (|ΔS|/S); and (d) the absolute fractional change of A (|ΔA|/A).

According to the present invention, the stimuli applied to the patient or subject may comprise any stimuli, including the sensory stimuli of taste, smell, and touch. In the preferred method of the present method, a background stimuli is first applied to the patient. The background stimuli includes a visual background stimulus and/or an audio background stimulus. Then, as shown in FIG. 7, the stimuli is modulated according to the activity of the sympathetic and/or parasympathetic branches of the subject's autonomic nervous system (see step 620).

The background stimuli may have default values for certain parameters, depending on the type of stimuli. For light and sound stimuli, frequency default values may be given. Background values for color brightness and sound loudness will preferably be adjusted to a minimum, and according to each individual subject, and his level of perception.

In the preferred embodiment, the visible color spectrum frequency range is taken to be approximately 380 nm to approximately 770 rim. This visible frequency range is divided into a low frequency color spectrum of approximately 380 rim (red) to approximately 530 nm (green) and a high frequency color spectrum of approximately 530 rim to approximately 770 nm (blue). The visual background stimulus generally consists of one of two colors. One default color has a hue within the high frequency color spectrum (i.e., approximately 490 rim), and the other default color has a hue within the low frequency color spectrum (i.e., approximately 600 rim).

In the preferred embodiment, the audible frequency range is taken to be approximately 25 Hz to approximately 1320 Hz. This audible frequency range is divided into a low frequency range from approximately 25 Hz to approximately 440 Hz, and a high frequency range from approximately 440 Hz to approximately 1320 Hz. One default sound has a frequency of approximately 880 Hz, which falls within the high frequency range, and the other default sound has a frequency of approximately 234 Hz, which falls within the low frequency range. In addition, the audio background stimulus comprises any type of sound, such as pink noise or violin sounds and has a given loudness.

In alternative embodiments, the background values for the sound stimulus is total silence (i.e., frequencies below 16 Hz) and total darkness.

In the present method, the stimuli is applied during a predefined time interval, which lasts at least 60 msec, referred to as an "action time" ($T_A$). When the stimuli consists of light, $T_A$ should not be shorter than 60 cosec to avoid fundamental frequencies above 16 I-Iz because these may trigger epileptic seizures. Other types of stimuli may have similar limitations.

The action time $T_A$ repeats itself after an interval designated as time off or $T_{OFF}$ during which the stimulus will return to its background values. In one embodiment, the stimuli modulation follows a cycle time equal to $T_A+T_{OFF}$. These time values are previously defined for each type of stimulus at the expert system in the stimuli modulation software 260.

When the stimuli is to be applied in synchronization with a biological cycle, there will be a time interval, referred to as "waiting time" ($T_W$), between a fiducial point of the biological cycle and the beginning of $T_A$. For example, when the stimuli is to be applied in synchronization with the cardiac cycle, $T_W$ is the interval between the RN fiducial point and the beginning of $T_A$. $T_A$ may end before the occurrence of the next RN+, fiducial point, resulting in an additional "gap time" (TG) between the end of an action time and the beginning of the next waiting time, starting at the next fiducial point. For example, if an NN interval is 783 msec, with a $T_W$, of a 200 ms; and $T_A$ of 180 msec, then $T_G=T_{NN}-(T_w,+T_A)=403$ msec.

It should be noted that, when a single stimulus is applied and modulated in synchronization with a biological cycle, the total cycle time for that particular stimulus will be equal to $Tv,+T_A+T_G$, where $T_W$ and $T_A$ have been previously defined, for each type of stimulus and/or its parameters within stimuli modulation software 260.

During each action time $T_A$, the stimuli are altered away from their default values (see step 620 in FIG. 7), according to two parameters referred to as the Stimulus Control Index (SCI) and the Directional Index (D). The Stimulus Control Index (SCI) determines the degree of change from the default for any stimulus parameter, and the Direction Index determines the direction of change from the default. In this example, there are four SCIs, including an SCI for color hue (θhu), an SCI for color brightness (θbr), an SCI for sound volume (θlo), and an SCI for sound frequency (θsf). The SCI is either the absolute fractional change of S or the absolute fractional change of A, and will be a number between 0 and 1. The Directional Index is either D+ or D−, depending on the increase or decrease of S or A. D(s) is D+ if S increases, D(s) is D− if S decreases, D(a) is D+ if A increases, and D(a) is D− if A decreases. These values are explained in more detail in the following example, which is explained with reference to FIG. 8.

In this example, the values for S, |ΔS|, A, |ΔA| are first calculated. As summarized in FIG. 8, the absolute fractional change of S is calculated, and this value determines the degree of the change from the default value of color hue and sound loudness. In other words, in this example, the SCI for color hue (θhu) and sound loudness (θlo) is |ΔS|/S.

The direction of this change is determined by the Directional Index for S. The Directional Index is D(s)+ if S increases from one time window to the next, and the Directional Index is D(s)− if S decreases from one time window to the next. If the light stimulus default value is between green and blue, D(s)+ indicates a change in color toward the blue region of the color spectrum, and D(s)− indicates a change in color toward the green region of the color spectrum. In addition, D(s)+ indicates an louder audio signal, and D(s)− indicates a quieter audio signal.

The absolute fractional change of A is also calculated, and, as summarized in FIG. 8, this value determines the value for the change from the default value of color brightness and sound frequency. In other words, in this example, the SCI for color brightness (θbr) and sound frequency (6sf) is 1 6 AI/A.

The direction of this change is determined by the Directional Index for A. The Directional Index is D(a)+ if A increases from one time window to the next, and the Directional Index is D(a)− if A decreases from one time window to the next. D(a)+ indicates an increase in brightness, and D(a)− indicates a decrease in brightness. In addition, D(a)+ indicates an increase in sound frequency, and D(a)− indicates a decrease in sound frequency.

Depending on these parameters, the stimuli shifts away from the default during $T_A$. Specifically, as set forth above, one default audio stimuli is a sound having a frequency of 234 Hz. The SCI for sound frequency, or θsf, is used to determine the change in frequency required. This is determined by multiplying θsf with the appropriate sound frequency scale range. The appropriate sound frequency scale range represents the maximum possible range in which the sound frequency may shift.

In this example, the sound frequency is limited to the low frequency range of 25 Hz to 440 Hz. Therefore, the sound frequency may shift from 234 Hz up to a maximum of 440 Hz (a scale range of 206 Hz) or may shift down from 234 Hz to a minimum of 25 Hz (a scale range of 209 Hz). Given θsf=0.5, therefore, two results may occur. If D(a)=D+ (due to an increase in A from the previous time window), the change in frequency would be a positive shift of 0.5(206 Hz) or 103 Hz. In other words, the sound frequency will shift up by 103 Hz to a sound frequency of 337 Hz, which is applied during $T_A$. If, on the other hand, D(a)=D− (due to a decrease in A from the previous time window), the change in frequency would be a negative shift of 0.5(209 Hz) or approximately 104 Hz. In other words, the sound frequency will shift down by 104 Hz to a sound frequency of 130 Hz, which is applied during $T_A$.

In this example, as shown in FIG. 8, the SCI for color hue ($\theta$hu) and sound loudness ($\theta$lo) are determined by the absolute fractional change in S, and the SCI for color brightness ($\theta$br) and sound frequency ($\theta$sf) are determined by the absolute fractional change in A. However, in alternative embodiments, the four SCIs may also be determined by any combination of the absolute fractional changes in S and A. Similarly, the Directional Index for any of the stimuli parameters may also be determined by any combination of changes in S and A. Appropriate scale ranges must be determined for each stimuli parameter to be modulated, and these scale ranges are stored within stimuli modulation software 260.

In alternative embodiments of the present invention, stimuli modulation is determined by further multiplying the SCI with a feedback index value (FIV) between 0 and 1 (0<FIV<1) depending on the effect intended. For example, if a positive feedback effect is intended, the stimuli modulation will be determined by SCI*FIV (e.g., FIV=0.8) for each D− that appears. In other words, stimuli shifts in the negative direction will be less than stimuli shifts in the positive direction. Similarly, if a negative feedback effect is intended, the stimuli modulation will be determined by SCI*FIV for each D+ that appears. An FIV of 1 indicates equal shifts in both directions.

FIV values will depend on the effect desired on sympathetic or parasympathetic activity. Initial assessment of a patient, based on baseline HRV measurement, together with accumulated experience and empirical data, will assist in determining FIV values at the expert system in stimuli modulation software 260 of the apparatus. Other alternative means of introducing a negative or positive feedback component in the applied and/or modulated stimuli may be incorporated in the present invention.

In an alternative method of the present invention, the stimuli is applied in coordination with cyclical activity of the body, such as with systole or diastole of the cardiac cycle and/or with inspiration or expiration of the breathing cycle.

It has been found that the balance between sympathetic and parasympathetic activity shifts or changes during periodic biological cycles, such as the menstrual and breathing cycles. There is also a circadian rhythm to ANS activity, wherein parasympathetic activity increases during the night and sympathetic activity increases during the day. In short biological cycles, like the heartbeat, a rise in sympathetic tone increases myocardial contractility and may prolong systolic ejection time. In addition, the QT interval in the electrocardiogram corresponding to the depolarization-repolarization cycle of the ventricles also increases if sympathetic activity increases. Sympathetic activity is related to the duration of systole and inspiration, and the diurnal period. Similarly, parasympathetic activity is related to the duration of diastole and expiration, and the nocturnal period. Due to these relationships, an alternative method of modulating the stimuli comprises establishing a veto for predefined sections or phases of a selected biological cycle. Halting or withdrawing the stimulus during predefined phases of a biological cycle optimizes the chances of selectively influencing the sympathetic and/or the parasympathetic branches of the ANS.

Stimuli may therefore be applied in coordination with systole to stimulate the sympathetic branch, while stimuli may be applied in coordination with diastole to stimulate the parasympathetic branch.

This synchronization is obtained by the following algorithm:
1) The mean value of a normal cardiac cycle (mNN) is obtained in milliseconds (cosec), from 30 prior successive NN intervals.
2) The time period between the fiducial point, calculated by the method shown above, and the end of the mechanical systole, is the systolic interval or Ts. This systolic interval can be calculated to a precision of a few milliseconds by the following equation:

$$Ts=512-(123.000/mNN) \quad (1)$$

3) To coordinate $T_A$ with Ts, the following equations are used:

$$Tw+T_A=TS\ Z \quad (2)$$

$$T_A 60 \quad (3)\ \text{(for light stimuli)}$$

where Tw is the waiting time in msec, between the fiducial point and the beginning of $T_A$. Any combinations for Tw and $T_A$ values are possible.

4) To coordinate $T_A$ with the cardiac interval following Ts, known as diastole, the following equations are used:

$$Tw=TS+Z \quad (4)$$

$$T_A<\_mNN-(T_s+180) \quad (5)$$

$$T_A Z 60 \quad (6)\ \text{(for light stimuli)}$$

The value of Z, given in msec, may differ for different stimuli acting on the same biological cycle. In the preferred method, the value of Z is at least 40 msec.

Alternatively, stimuli may be applied in coordination with inspiration to stimulate the sympathetic branch, while stimuli is applied in coordination with expiration to stimulate the parasympathetic branch.

Stimuli coordination with the breathing cycle may require monitoring the lung movements in order to determine the beginning and the end of the inspiration period, as well as the total duration of the respiratory cycle. On average, the breathing cycle $T_B$, is four times longer than the cardiac cycle and generally lasts more than 3000 msec. The inspiration period generally lasts around 1000 msec. Therefore, even if the breathing monitoring device may not be highly accurate, synchronizing stimuli application and/or modulation lasting around 200 or 300 msec, for example, with relatively long inspiration or expiration periods, will not present technical difficulties. Devices for monitoring the breathing cycle include chest belts with, for example, piezo-electric sensors. Another type of monitor includes finger photopletismographic devices which are sensitive to venous pressure oscillations coupled with the mechanical wave generated by the lung's periodical volume changes during the breathing cycle. After eliminating noise by proper filtering, the first derivative of the breathing wave form curve will identify the beginning and end of the inspiration slope. Once the respiratory fiducial point at the beginning of the inspiration phase is obtained, average values for the breathing cycle ($mT_B$) together with its two main phases, can then be calculated. Stimuli coordination with breathing can be achieved with the following algorithm, with values given in msec. To coordinate T,4 with the inspiration period T, the following equations are used:

$$Tw+T_A=T_i Z \quad (7)$$

$$T_A \geq 60 \quad (8)\ \text{(for light stimuli)}$$

To coordinate $T_A$ with the expiration period the following equations are used:

$$Tw = T_f + Z \quad (9)$$

$$T_A \leq mTB - (TW + Z) \quad (10)$$

$$T_A \geq 60 \quad (11) \text{ (for light stimuli)}$$

where $T_w$ is the time interval between the respiratory fiducial point and the beginning of the action time $T_A$, in msec and $mT_B$ is the average $T_B$ value of at least 5 breathing cycles, in msec. The value of Z may change according to the case and in the preferred method Z is at least 100 msec.

Simultaneous coordination with the cardiac and respiratory cycle is also possible. In order to influence sympathetic activity equations (1), (2), and (7) are used. $T_A$ will be given the same value in the above algorithms. These particular combinations could be proven to be very useful in patients suffering from asthma. Similarly, in order to influence the parasympathetic activity equations (1), (4), (5), (9), and (10) are used, giving $T_A$ the same value.

One aspect of the invention relates to the timing of application of the stimuli. In a further alternative method of the present invention, for example, the stimuli may be applied at certain times that are significant to sympathetic or parasympathetic activities. As stated above, it is known that the sympathetic branch of the autonomic nervous system is more active during the day, and that the parasympathetic branch of the autonomic nervous system is more active at night. Therefore, one aspect of the invention is to apply sensory stimuli either during the day or during the night depending on which branch of the autonomic nervous system to be stimulated or the particular health situation to be addressed.

It should also be noted that the time of day also has an effect on HRV measurement. HRV measurements for clinical evaluation may require short time ECG recordings, including at least nine hundred RR intervals. Although these recordings may be taken at any time, they should be renormalized for a predefined hour, such as 12 am. To compare HRV changes in one patient before and after treatment, more accurate results will be obtained if the ECG recordings of that patient are taken having the same length and at the same hour in the day.

The following examples are intended to illustrate the method according to the present invention. However, they are not intended to limit the scope of the invention as set forth in the appended claims.

Example 1

In this example, a subject is treated for insomnia and/or stress by stimulating or increasing parasympathetic activity of the autonomic nervous system. It should be noted that an evaluation of the patient's baseline HRV may indicate that rather than increasing parasympathetic activity, sympathetic activity should be decreased. Alternatively, the patient's condition may require stimulation of both parasympathetic and sympathetic activity, but wherein parasympathetic activity should be increased more than sympathetic activity.

As described above, the patient's ECG is first recorded before the beginning of the treatment to make a preliminary diagnosis of the patient and to determine generally what method of treatment is indicated. During treatment, the patient's ECG is continuously obtained from which successive power spectrum (PS) variability curves are continuously derived from successive and overlapping time windows, wherein each time window spans 120 heartbeats (i.e., k=4 (default value) and N=30 k=120 heartbeats) or approximately 2 minutes of the ECG recording. The beginning of each window is separated from beginning of the previous window by M=10 heartbeats or approximately 10-second intervals.

In this example, the region of interest is the frequency range over 0.15 Hz, which, as stated above, is thought generally to be a reflection of parasympathetic activity. The stimuli is determined based on changes in the area below the power spectrum curve in this region. An increase in area reflects an increase in parasympathetic activity, and a decrease in area reflects a decrease in parasympathetic activity. In one embodiment of the present invention, feedback of this information comprises modulation of light and/or sound stimuli which follows a positive feedback correlation with the measured changes in the area under the curve and in the height of the highest peak in this region.

Because a parasympathetic effect is intended, the visual stimuli will comprise colors in the range between green and violet. The audio stimuli will comprise sounds in the low frequency range between approximately 25 and approximately 440 Hz.

The background default visual stimulus is a blue-green color of 490 run. This color is displayed on a TV or computer screen. The area S under the variability curve in the region of interest is continuously monitored. If this area increases, the color of at least a part of the screen is shifted toward the violet end of the color spectrum during $T_A$, and if this area decreases, the color is shifted toward the green end of the color spectrum during $T_A$. The SCI for color hue ($\theta hu$) is $|\Delta S|/S$. Because a positive feedback effect is desired, color shifts toward the green end of the spectrum will be smaller than color shifts toward the violet end. In this example, the FIV=0.8, and for every D–, the stimuli shift is determined 4 the product of FIV and SCI.

The central tendency peak or the height of the curve at its peak A in the region of interest is also continuously monitored, and as the height of the peak increases, the brightness of the color is increased, and as the height of the peak decreases, the brightness is decreased, albeit in smaller proportion than the increase in intensity. The SCI for color brightness ($\theta br$) is $|\Delta A|/A$. Again, for every D–, the stimuli shift is determined by the product of FIV and SCI.

The background auditory stimulus is a sound having a frequency of 234 Hz, which is within the low frequency range between 25 Hz and 440 Hz. As the area S under the variability curve in the region of interest increases, the frequency of the sound during $T_A$ is decreased, and as the area S decreases, the frequency of the sound is increased, albeit in smaller proportion than the decreases in pitch. In addition, as the height of the central tendency peak above 0.15 Hz increases, the loudness of the sound is decreased, and as the height of the central tendency peak above 0.15 Hz decreases, the loudness of the sound is increased, albeit in smaller proportion than the decreases in loudness. Modulation of loudness is determined in the same way as the modulation of brightness, which is described above.

In addition, the stimuli duration $T_A$ may be constant or may vary from approximately 0.06 seconds to approximately 0.18 seconds. The default duration is approximately 0.12 sec. As parasympathetic activity increases, $T_A$ is increased, and as parasympathetic activity decreases, $T_A$ is decreased, albeit in smaller proportion than the increases in duration. In other words, in this example there is an SCI for $T_A$ which is equal to $|\Delta S|/S$. T(off), which represents the time period between consecutive auditory stimuli, may be determined in at least one of the following two ways.

In one embodiment of the method, $T_A$ is not synchronized with any biological cycle, and T(off) may be any arbitrary predefined time value.

In an alternative embodiment, the stimuli is applied during a predefined phase of a physiological cycle. As explained previously for example, the stimuli may be synchronized with the cardiac cycle, using the R fiducial point of the QRS complex as a reference. To increase parasympathetic activity, the stimuli will be applied during the latter or diastolic phase of the cardiac cycle. The delay ($T_W$) between the fiducial point in the QRS complex of the ECG signal and the starting point of the stimuli is calculated according to equations (1), (4), (5), and (6) explained above.

Example 2

In this example, a subject is treated for migraines and/or poor mental concentration by assisting the autonomic nervous system in stimulating or increasing sympathetic activity. Again, alternative treatments may be possible. The subject's baseline heart rate variability is initially determined by time domain and spectral analysis as described above.

From the patient's ECG, successive PS variability curves are obtained from successive and overlapping time windows, wherein each time window spans 90 heartbeats (i.e., k=3 and N=30 k=90 heartbeats) or approximately 1.5 minutes of the ECG recording. The beginning of each window is separated from the beginning of the previous one by M=4 heartbeats, which is approximately 4 seconds. In this example, the power spectrum region of interest is below 0.15 Hz, and the stimuli is determined based on changes in the area and in the height of the highest peak in this region.

Because a sympathetic effect is intended, the visual stimulus will comprise colors ranging from green to red, and the audio stimulus will range from approximately 440 Hz to approximately 1320 Hz.

The background visual stimulus is an orange color of approximately 600 rim, which is a color between green and red. This color is displayed on a TV or computer screen. The area S under the variability curve in the region of interest is continuously monitored. If this area increases; the color of at least part of the screen is shifted toward the red end of the color spectrum, and if this area decreases, the color of at least part of the screen is shifted toward the green end of the color spectrum. Color shifts toward the green end of the spectrum are smaller than color shifts toward the red end. In this example, the SCI for color hue (θhu) is $|\Delta S|/S$, and FIV=0.7.

The height of the central tendency peak A in the region of interest is also continuously monitored, and as the height of the peak increases, the brightness or intensity of the color is increased, and as the height of the peak decreases, the intensity is decreased, albeit in smaller proportion than the increase in intensity. In this example, SCI for color brightness (θbr) is $|\Delta A|/A$.

The background auditory stimulus is a sound having a frequency of 880 Hz. As sympathetic activity increases, the frequency of the sound is increased, and as sympathetic activity decreases, the frequency of the sound decreases, albeit in smaller proportion than the increases in pitch. The SCI value for sound frequency (θsf) is $|\Delta S|/S$ In addition, as the height of the central tendency peak A below 0.15 Hz increases, the loudness of the sound is increased, and as the height of the central tendency peak below 0.15 Hz decreases, the loudness of the sound is decreased, albeit in small proportion than the decreases in loudness. The SCI value for sound loudness (θlo) is $|\Delta A|/A$ In addition, the stimuli duration $T_A$ may be constant or may vary from approximately 0.12 seconds to approximately 0.16 seconds. The default duration is approximately 0.14 sec. As sympathetic activity increases, $T_A$ is decreased, and as sympathetic activity decreases, $T_A$ is increased, albeit in smaller proportion than the decreases in duration. In other words, the SCI for $T_A$ is $|\Delta S|/S$. T(off), which represents the time period between consecutive stimuli, may be determined in at least one of the following two ways.

As described above in Example 1, in one embodiment of the present invention, $T_A$ is not synchronized with any biological cycle, and T(off) may have any arbitrary predetermined time value.

In another embodiment of the present method, the stimuli is applied during a predefined phase of a physiological cycle, such as the cardiac cycle. To increase sympathetic activity, the stimuli will be applied during the early or systolic phase of the cardiac cycle, where the delay $T_W$ between the fiducial point in the QRS complex of the ECG signal and the starting point of the stimuli will be calculated according to equations (1) and (2) explained above.

It will be readily apparent to those in the art that variations of this method and modifications of this apparatus are possible which fall within the scope of the appended claims.

What is claimed is:

1. A method comprising:
    applying at least one stimulus to a subject, wherein the at least one stimulus is modulated by at least one variable stimulus parameter;
    monitoring at least one subject parameter of the subject;
    separately analyzing at least one of sympathetic and parasympathetic activity of the subject based on the monitored subject parameter; and
    controlling the application of the at least one stimulus by modulating the at least one variable stimulus parameter in accordance with separate analysis from the sympathetic activity or the parasympathetic activity of the subject.

2. The method of claim 1, wherein the at least one stimulus affects afferent neural pathways of the subject.

3. The method of claim 1, wherein application of the at least one stimulus and monitoring of the at least one subject parameter are performed non-invasively.

4. The method of claim 1, wherein the at least one variable stimulus parameter is selected to affect at least one type of sensorial receptors of the subject.

5. The method of claim 4, further comprising:
    applying a second stimulus to the subject, wherein the second stimulus is modulated by at least a second variable stimulus parameter.

6. The method of claim 5, wherein the at least one variable stimulus parameter and the second variable stimulus parameter each comprise at least one of amplitude and frequency.

7. The method of claim 6, wherein the at least one stimulus comprises light and the second stimulus comprises sound.

8. The method of claim 1, wherein the at least one subject parameter comprises at least one of a physiological, cognitive, and behavioral activity of the subject.

9. The method of claim 1, wherein the monitoring is accomplished prior to application of stimuli.

10. The method of claim 9, further comprising:
    discontinuing monitoring during application of the at least one stimulus.

11. The method according to claim 1, wherein said monitoring occurs during application of the stimuli.

12. The method according to claim 11, wherein said controlling comprises continuously adjusting said stimuli application in response to the monitored subject parameter.

13. The method of claim 1, wherein the at least one subject parameter comprises cardiovascular activity.

14. The method of claim 13, wherein the at least one subject parameter comprises electrical currents related to heart contraction.

15. The method of claim 14, wherein the at least one subject parameter is monitored by an electrocardiograph.

16. The method of claim 1, wherein the at least one subject parameter comprises an electrophysiological parameter, the controlling comprising:
converting the electrophysiological parameter to a heart rate variability measurement comprising a separate frequency domain analysis of sympathetic activity changes and of parasympathetic activity changes; and
modulating the at least one variable stimulus parameter in response to changes in the heart rate variability measurement, wherein changes are selected from a group comprising the analyzed sympathetic activity changes, the analyzed parasympathetic activity changes, and a predefined mathematical relationship between the sympathetic and parasympathetic activity.

17. A method for affecting the autonomic nervous system of a subject comprising:
measuring the heart rate variability of the subject;
separately analyzing at least one of sympathetic and parasympathetic activity of the subject based on the heart rate variability measurement; and
applying at least one stimulus to the subject in response to at least one of the sympathetic and parasympathetic activity of the subject.

18. An apparatus for affecting the autonomic nervous system of a subject comprising:
means for obtaining a plurality of power spectra, wherein each power spectrum depicts heart rate variability of the subject as a function of frequency, and the power spectra are obtained over predetermined time windows;
means for measuring area under each power spectrum in at least one predetermined frequency range, and the maximum value of variability in the predetermined frequency range; and
modulating means for modulating a first parameter of a stimulus to be applied to the subject based on a change in the area between two power spectra and for modulating a second parameter of the stimulus based on a change in the maximum value of variability between the two power spectra.

19. The method of claim 1, wherein modulating the at least one variable stimulus parameter comprises altering the variable stimulus parameter away from a default value in a direction and amplitude defined by a preselected function.

20. The method of claim 1, wherein modulating the at least one variable stimulus parameter comprises modulating the at least one variable stimulus parameter in coordination with a preselected biological cycle of the subject.

21. A computer-readable storage device having instructions stored thereon, execution of which, by a computing device, causes the computing device to perform operations comprising:
applying at least one stimulus to a subject, wherein the at least one stimulus is modulated by at least one variable stimulus parameter;
monitoring at least one subject parameter of the subject;
separately analyzing at least one of sympathetic and parasympathetic activity of the subject based on the subject parameter; and
controlling the application of the at least one stimulus by modulating the at least one variable stimulus parameter in accordance with separate analysis from the sympathetic activity or the parasympathetic activity of the subject.

22. The computer-readable storage device of claim 21, wherein the at least one stimulus affects afferent neural pathways of the subject.

23. The computer-readable storage device of claim 21, wherein application of the at least one stimulus and monitoring of the at least one subject parameter are performed non-invasively.

24. The computer-readable storage device of claim 21, wherein the at least one variable stimulus parameter is selected to affect at least one type of sensorial receptors of the subject.

25. The computer-readable storage device of claim 24, the operations further comprising:
applying a second stimulus to the subject, wherein the second stimulus is modulated by at least a second variable stimulus parameter.

26. The computer-readable storage device of claim 25, wherein the at least one variable stimulus parameter and the second variable stimulus parameter each comprise at least one of amplitude and frequency.

27. The computer-readable storage device of claim 26, wherein the at least one stimulus comprises light and the second stimulus comprises sound.

28. The computer-readable storage device of claim 21, wherein the at least one subject parameter comprises at least one of a physiological, cognitive, and behavioral activity of the subject.

29. The computer-readable storage device of claim 21, wherein the monitoring is accomplished prior to application of stimuli.

30. The computer-readable storage device of claim 29, the operations further comprising:
discontinuing monitoring during application of the at least one stimulus.

31. The computer-readable storage device of claim 21, wherein the at least one subject parameter comprises cardiovascular activity.

32. The computer-readable storage device of claim 31, wherein the at least one subject parameter comprises electrical currents related to heart contraction.

33. The computer-readable storage device of claim 32, wherein the at least one subject parameter is monitored by an electrocardiograph.

34. The computer-readable storage device of claim 21, wherein the at least one subject parameter comprises an electrophysiological parameter, the controlling comprising:
converting the electrophysiological parameter to a heart rate variability measurement comprising a separate frequency domain analysis of sympathetic activity changes and of parasympathetic activity changes; and
modulating the at least one variable stimulus parameter in response to changes in the heart rate variability measurement, wherein changes are selected from a group comprising the analyzed sympathetic activity changes, the analyzed parasympathetic activity changes, and a predefined mathematical relationship between the sympathetic and parasympathetic activity.

35. The computer-readable storage device of claim 21, wherein modulating the at least one variable stimulus parameter comprises altering the variable stimulus parameter away from a default value in a direction and amplitude defined by a preselected function.

36. The computer-readable storage device of claim 21, wherein modulating the at least one variable stimulus parameter comprises modulating the at least one variable stimulus parameter in coordination with a preselected biological cycle of the subject.

37. An apparatus comprising:
a patient monitor device configured to monitor at least one subject parameter of a subject and to separately analyze at least one of sympathetic and parasympathetic activity of the subject based on the subject parameter; and
a stimuli modulating unit configured to:
apply at least one stimulus to the subject, wherein the at least one stimulus is modulated by at least one variable stimulus parameter, and
control the application of the at least one stimulus by modulating the at least one variable stimulus parameter in accordance with separate analysis from the sympathetic activity or the parasympathetic activity of the subject.

38. The apparatus of claim 37, wherein the at least one stimulus affects afferent neural pathways of the subject.

39. The apparatus of claim 37, wherein application of the at least one stimulus and monitoring of the at least one subject parameter are performed non-invasively.

40. The apparatus of claim 37, wherein the at least one variable stimulus parameter is selected to affect at least one type of sensorial receptors of the subject.

41. The apparatus of claim 40, wherein the stimuli modulating unit is further configured to apply a second stimulus to the subject, wherein the second stimulus is modulated by at least a second variable stimulus parameter.

42. The apparatus of claim 41, wherein the at least one variable stimulus parameter and the second variable stimulus parameter each comprise at least one of amplitude and frequency.

43. The apparatus of claim 42, wherein the at least one stimulus comprises light and the second stimulus comprises sound.

44. The apparatus of claim 37, wherein the at least one subject parameter comprises at least one of a physiological, cognitive, and behavioral activity of the subject.

45. The apparatus of claim 37, wherein the monitoring is accomplished prior to application of stimuli.

46. The apparatus of claim 45, wherein the stimuli modulating unit is further configured to discontinue monitoring during application of the at least one stimulus.

47. The apparatus of claim 37, wherein the at least one subject parameter comprises cardiovascular activity.

48. The apparatus of claim 37, wherein the at least one subject parameter comprises electrical currents related to heart contraction.

49. The apparatus of claim 38, wherein the at least one subject parameter is monitored by an electrocardiograph.

50. The apparatus of claim 37, wherein the at least one subject parameter comprises an electrophysiological parameter,
wherein the patient monitor device is further configured to convert the electrophysiological parameter to a heart rate variability measurement comprising a separate frequency domain analysis of sympathetic activity changes and of parasympathetic activity changes, and
wherein the stimuli modulating unit is further configured to modulate the at least one variable stimulus parameter in response to changes in the heart rate variability measurement, wherein changes are selected from a group comprising the analyzed sympathetic activity changes, the analyzed parasympathetic activity changes, and a predefined mathematical relationship between the sympathetic and parasympathetic activity.

51. The apparatus of claim 37, wherein modulating the at least one variable stimulus parameter comprises altering the variable stimulus parameter away from a default value in a direction and amplitude defined by a preselected function.

52. The apparatus of claim 37, wherein modulating the at least one variable stimulus parameter comprises modulating the at least one variable stimulus parameter in coordination with a preselected biological cycle of the subject.

53. The method according to claim 1, wherein said controlling comprises continuously adjusting said stimuli application in response to the monitored subject parameter.

* * * * *